(12) United States Patent
Guerrera et al.

(10) Patent No.: US 12,023,807 B2
(45) Date of Patent: Jul. 2, 2024

(54) SYSTEM AND METHOD FOR CONTROLLING A POSITION OF AN ARTICULATED ROBOTIC ARM

(71) Applicant: Corindus, Inc., Waltham, MA (US)

(72) Inventors: Stephen Guerrera, Holliston, MA (US); Robert Elden, Cambridge, MA (US); Steven J. Blacker, Framingham, MA (US); Per Bergman, West Roxbury, MA (US); Saeed Sokhanvar, Belmont, MA (US); Eric Klem, Lexington, MA (US)

(73) Assignee: Corindus, Inc., Newton, MA (US)

( * ) Notice: Subject to any disclaimer, the term of this patent is extended or adjusted under 35 U.S.C. 154(b) by 793 days.

(21) Appl. No.: 17/098,165

(22) Filed: Nov. 13, 2020

(65) Prior Publication Data

US 2021/0060767 A1 Mar. 4, 2021

Related U.S. Application Data

(63) Continuation of application No. 15/946,917, filed on Apr. 6, 2018, now Pat. No. 10,864,629, which is a
(Continued)

(51) Int. Cl.
| | |
|---|---|
| *B25J 9/16* | (2006.01) |
| *A61B 6/00* | (2006.01) |
| *A61B 6/04* | (2006.01) |
| *A61B 6/12* | (2006.01) |
| *A61B 6/46* | (2024.01) |

(Continued)

(52) U.S. Cl.
CPC ............. *B25J 9/161* (2013.01); *A61B 6/0407* (2013.01); *A61B 6/12* (2013.01); *A61B 6/4405* (2013.01); *A61B 6/4458* (2013.01); *A61B 6/4464* (2013.01); *A61B 6/467* (2013.01); *A61B 6/547* (2013.01); *B25J 9/16* (2013.01); *B25J 9/1679* (2013.01); *G21F 3/00* (2013.01); *G21F 7/066* (2013.01); *G21F 7/068* (2013.01); *A61B 6/462* (2013.01); *G05B 2219/39101* (2013.01);
(Continued)

(58) Field of Classification Search
CPC .. B25J 9/161; B25J 9/16; B25J 9/1679; A61B 6/0407; A61B 6/12; A61B 6/4405; A61B 6/4458; A61B 6/4464; A61B 6/467; A61B 6/547; A61B 6/462; G21F 3/00; G21F 7/066; G21F 7/068; G05B 2219/39101; G05B 2219/39129; G05B 2219/45118
See application file for complete search history.

(56) References Cited

U.S. PATENT DOCUMENTS

| | | |
|---|---|---|
| 6,726,675 B1 | 4/2004 | Beyar |
| 7,276,044 B2 | 10/2007 | Ferry et al. |

(Continued)

*Primary Examiner* — Rachid Bendidi

(57) ABSTRACT

A system for controlling the position of an articulated robotic arm includes a robotic catheter procedure system having the articulated robotic arm and a controller coupled to the articulated robotic arm. The system further includes a patient table positioned proximate to and separate from the articulated robotic arm and a tracking system coupled to the controller and configured to measure a change in a position of the patient table. The controller is configured to adjust the position of the articulated robotic arm based on the measured change in position of the patient table.

12 Claims, 14 Drawing Sheets

Related U.S. Application Data continuation-in-part of application No. 14/732,845, filed on Jun. 8, 2015, now Pat. No. 9,943,958, which is a continuation-in-part of application No. 14/212,143, filed on Mar. 14, 2014, now Pat. No. 9,070,486.

(60) Provisional application No. 61/791,707, filed on Mar. 15, 2013.

(51) Int. Cl.
  *G21F 3/00* (2006.01)
  *G21F 7/06* (2006.01)

(52) U.S. Cl.
  CPC .............. *G05B 2219/39129* (2013.01); *G05B 2219/45118* (2013.01)

(56) References Cited

U.S. PATENT DOCUMENTS

| | | | |
|---|---|---|---|
| 7,766,856 B2 | 8/2010 | Ferry et al. | |
| 7,887,549 B2 | 2/2011 | Wenderow et al. | |
| 8,382,372 B2 | 2/2013 | Maschke | |
| 8,399,871 B2 | 3/2013 | Beyar et al. | |
| 9,095,681 B2 | 8/2015 | Wenderow et al. | |
| 2005/0129181 A1* | 6/2005 | Shinoda | A61B 6/547 378/209 |
| 2005/0234327 A1 | 10/2005 | Saracen et al. | |
| 2008/0300458 A1* | 12/2008 | Kim | A61B 34/73 600/118 |
| 2009/0046146 A1 | 2/2009 | Hoyt | |
| 2009/0234444 A1 | 9/2009 | Maschke | |
| 2010/0073150 A1* | 3/2010 | Olson | A61B 34/74 340/407.1 |
| 2010/0145358 A1 | 6/2010 | Maschke | |
| 2011/0174997 A1 | 7/2011 | Rees | |
| 2011/0238082 A1 | 9/2011 | Wenderow et al. | |
| 2012/0038307 A1* | 2/2012 | Ahn | B23Q 15/22 318/640 |
| 2012/0179167 A1 | 7/2012 | Wenderow et al. | |
| 2012/0323233 A1 | 12/2012 | Maguire et al. | |
| 2013/0066135 A1 | 3/2013 | Rosa et al. | |
| 2014/0284503 A1 | 9/2014 | Stevick et al. | |

\* cited by examiner

SYSTEM AND METHOD FOR CONTROLLING A POSITION OF AN ARTICULATED ROBOTIC ARM

CROSS-REFERENCE TO RELATED PATENT APPLICATIONS

This application is a continuation of U.S. patent application Ser. No. 15/946,917 entitled SYSTEM AND METHOD FOR CONTROLLING A POSITION OF AN ARTICULATED ROBOTIC ARM filed Apr. 6, 2018, which is a continuation-in-part of U.S. patent application Ser. No. 14/732,845 entitled SYSTEM AND METHOD FOR CONTROLLING A POSITION OF AN ARTICULATED ROBOTIC ARM filed Jun. 8, 2015, now U.S. Pat. No. 9,943,958, which is a continuation-in-part of U.S. patent application Ser. No. 14/212,143 entitled RADIATION SHIELDING COCKPIT WITH ARTICULATED ROBOTIC ARM filed Mar. 14, 2014, now U.S. Pat. No. 9,070,486, which claims priority to U.S. Provisional Application No. 61/791,707 entitled RADIATION SHIELDING COCKPIT WITH ARTICULATED ROBOTIC ARM filed Mar. 15, 2013, all of which are incorporated herein by reference in their entirety.

BACKGROUND

There are systems for the performance of medical procedures in which a percutaneous device is inserted into a human patient with the guidance of an X-ray image using a mechanism held adjacent to the patient by a robotic arm and the mechanism is controlled from a remote cockpit which provides shielding to the operator of the system from the radiation generated in obtaining the X-ray image. The arm has typically been attached to the patient table by a rail and removed from the rail and placed on the floor or placed in other storage between procedures.

SUMMARY

In accordance with an embodiment, a system for controlling the position of an articulated robotic arm includes a robotic catheter procedure system having the articulated robotic arm and a controller coupled to the articulated robotic arm. The system further includes a patient table positioned proximate to and separate from the articulated robotic arm and a tracking system coupled to the controller and configured to measure a change in a position of the patient table. The controller is configured to adjust the position of the articulated robotic arm based on the measured change in position of the patient table.

In accordance with another embodiment, a system for controlling the position of an articulated robotic arm includes a robotic catheter procedure system having the articulated robotic arm and a controller coupled to the articulated robotic arm. The system further includes a patient table positioned proximate to and separate from the articulated robotic arm and a tracking system coupled to the controller and configured to measure a change in a position of a fiducial target. The controller is configured to adjust the position of the articulated robotic arm based on the measured change in position of the fiducial target.

In accordance with another embodiment, a system for controlling the position of an articulated robotic arm includes a robotic catheter procedure system having the articulated robotic arm, a controller coupled to the articulated robotic arm and at least one device. The system further includes a patient table positioned proximate to and separate from the articulated robotic arm and a tracking system coupled to the controller and configured to measure a change in a position of the device in the robotic catheter procedure system. The controller is configured to adjust the position of the articulated robotic arm based on the measured change in position of the device in the robotic catheter procedure system.

In accordance with another embodiment, a system for controlling the position of an articulated robotic arm includes a support having a top surface, a set of wheels, and a connector. The system further includes the articulated robotic arm positioned on the top surface of the support and a patient table positioned proximate to the support, wherein the connector is connected to patient table so that a change in position of the patient table causes a change in position of the support.

In accordance with another embodiment, a system for controlling the position of an articulated robotic arm includes a patient table, an articulated robotic arm mounted to a surface proximate to the patient table, the articulated robotic arm positioned separate from the patient table and a connector connected to the patient table and the articulated robotic arm so that a change in position of the patient table causes a change in position of the articulated robotic arm.

DETAILED DESCRIPTION

Figure 1A:
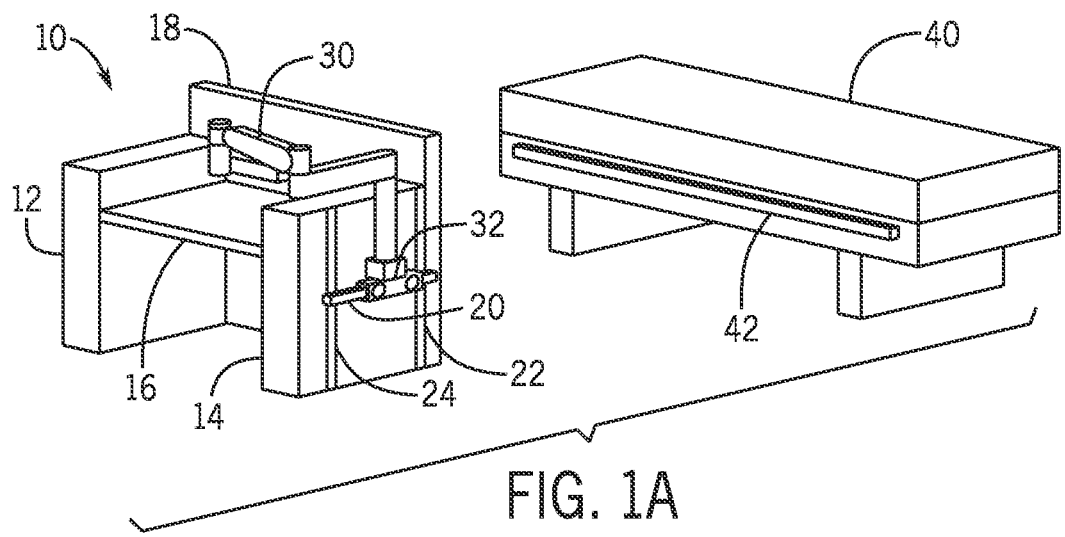
FIG. 1A is a perspective view of a radiation shielding cockpit with an articulated robotic arm attached and an adjacent patient table in accordance with an embodiment.

Referring to FIG. 1A, a radiation shielding cockpit 10 is shown with a left side wall 12, a right side wall 14, a horizontal work table 16 and a front wall 18. Attached to the right side wall 14 is a mounting rail 20. This attachment is via right vertical rail 22 and left vertical rail 24, both of which are attached to the right wall 20. An articulated robotic arm 30 is attached to the mounting rail 20 via an articulated robotic arm mounting bracket 32. The articulated robotic arm 30 is in a stored position with most of its structure lying above the cockpit work table 16. Adjacent the radiation shielding cockpit 10 is a patient table 40 which has an articulated robotic arm mounting bracket 42. In one embodiment to put the system into use and perform a procedure the articulated robotic arm 30 is removed from the mounting rail 20 and attached to the patient table mounting rail 42. After a procedure is completed the articulated robotic arm 30 may be removed from the patient table mounting rail 42 and attached to the cockpit mounting rail 20 thus facilitating its storage out of the way of medical personal who perform their functions such as transport of the patient and preparing the patient table to receive a patient in the close vicinity of the patient table 40.

Figure 1B:
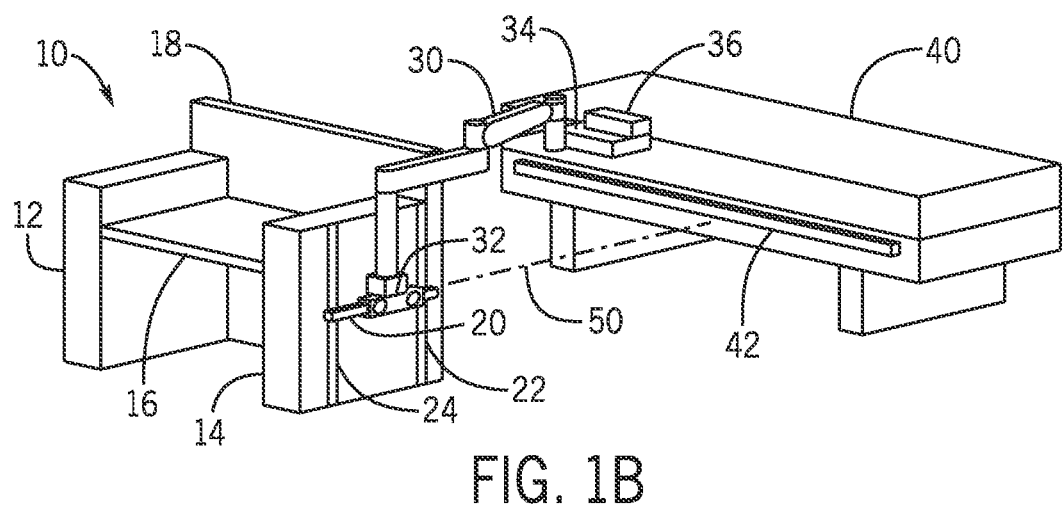
FIG. 1B is a perspective view of a radiation shielding cockpit with an articulated robotic arm attached and deployed above an adjacent patient table in accordance with an embodiment.

Referring to FIG. 1B, a similar arrangement to that of FIG. 1B is shown with the item numbers having the same meaning. However, in this case the articulated robotic arm 30 is dynamically mounted to the radiation shielding cockpit 10. The articulated robotic arm 30 includes a mechanism which allows it to track any movements of the patient table 40, particularly in the xy or horizontal plane, and deploy its drive motor mounting base 34 and its attached cassette 36 in a proper orientation to the patient table 40 and therefore the patient (not illustrated). The tracking mechanism of the articulated robotic arm 30 may be instructed by a wireless positioning signal 50. In this embodiment the patient table mounting rail 42 is not used.

Articulated robotic arm 30 may also be controlled in the z direction and automatically adjusted in the vertical z direction by a controller to ensure that the height of the robotic arm 30 is constant with respect to the patient table 40 or patient. This would allow for a constant positioning of a robotic catheter drive with the patient. If the patient moved for example on the table the robotic arm could automatically adjust so that the guide wire or catheter does not move relative to the patient in an undesirable manner.

Although not shown in FIG. 1A or 1B, cockpit 10 may include radiation shields that extend over the walls of the cockpit. In one embodiment, two of the walls have a transparent radiation shield extending upward from the walls, while the third wall remains free of a shield so that the robotic arm may be rotated into the center portion of the cockpit when not in use. Alternatively, a shield may be located on the third wall and removable or may be lowered to allow at least a portion of the robotic arm to swing into the center area of the cockpit when it is desired to store the robotic arm when not in use.

Figure 2:
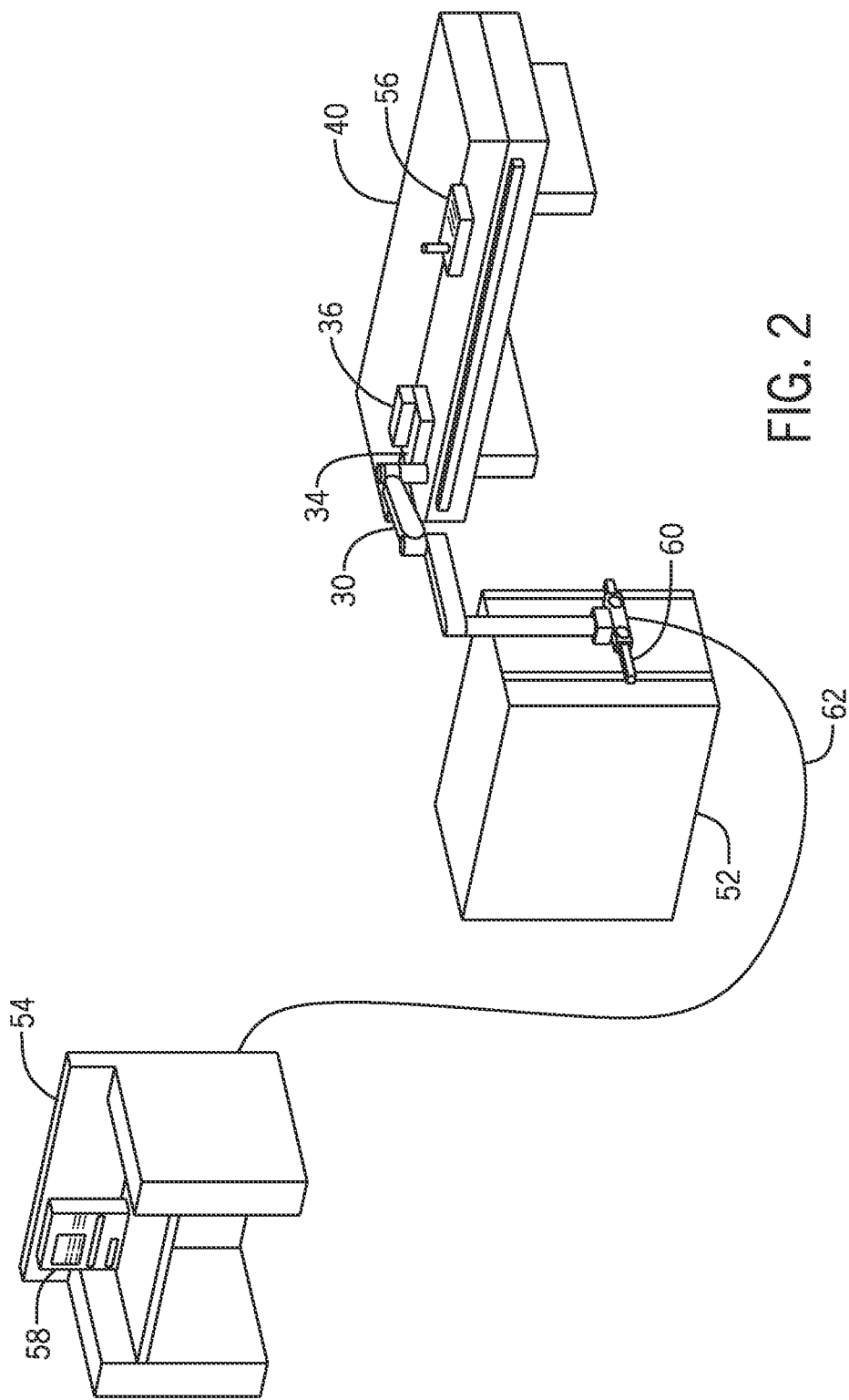
FIG. 2 is a perspective view of a catheter procedure system including a system for controlling a position of an articulated robotic arm in accordance with an embodiment.

In another embodiment, the articulated robotic arm 30 may be mounted to a support that is separate from the radiation shielding cockpit 10 and the patient table 40. FIG. 2 is a perspective view of a catheter procedure system including a system for controlling a position of an articulated robotic arm in accordance with an embodiment. In FIG. 2, an articulated robotic arm 30 is mounted to a support 52 using, for example, a mounting rail 60 on a side of support 52. In other embodiments, the articulated robotic arm 30 may be mounted to support 52 using other known mounting methods. In another embodiment, the articulated robotic arm 30 may be mounted on the top of the support 52. The support 52 may be any structure to which the articulated robotic arm 30 may be mounted such as, for example, a table, a cart with wheels, etc. In one embodiment, support 52 is configured to be moved in a horizontal or vertical direction. For example, the support 52 may include a moveable portion (not shown) and the articulated robotic arm 30 may be mounted to the moveable portion. A drive motor mounting base 34 and cassette 36 are mounted to an end of the articulated robotic arm 30. Cassette 34 is supported by the articulated robotic arm 30 and used to perform a catheter based medical procedure.

A control console or workstation 54 is in communication with the articulated robotic arm 30, support 52, drive motor mounting base 34 and cassette 36 to provide control signals to control the various functions of the articulated robotic arm 30, support 52, drive motor mounting base 34 and cassette 36. Control console 54 may be in communication with articulated robotic arm 30, support 52, drive motor mounting base 34 and cassette 36 via a communication link 62 that may be a wireless connection, cable connection, or any other means capable of allowing communication to occur between the components. Control console 54 includes a user interface 58 configured to receive user inputs to operate various components. User interface 58 includes controls (for example, a touch screen, one or more joysticks, buttons, display monitors, etc.) that allow a user to control the components to perform a catheter based medical procedure. In one embodiment, control console 54 may also be a radiation shielding cockpit and include radiation shields.

The articulated robotic arm 30 and support 52 are positioned adjacent to a patient table 40. Patient table 40 includes a patient table user interface 56 that is used to control the movement and position of the patient table 40. Patient table user interface 56 is configured to receive user inputs and includes controls such as, for example, one or more joysticks, buttons, etc. Patient table user interface 56 may be used to adjust the position of the patient table 40 by causing movement of the patient table 40 in a horizontal direction or a vertical direction.

Control console 54 is also in communication with the patient table 40. In an embodiment, control console 54 and patient table 40 communicate so that the movement of the patient table 40 may be tracked and the position of the articulated robotic arm 30 automatically adjusted to be in the proper orientation with respect to the patient table 40. In another embodiment, the position of support 52 (or a moveable portion of support 52) may be automatically adjusted so that the articulated robotic arm 30 is in the proper orientation with respect to the patient table 40. Control console 54 may be in communication with the patient table 40 via a communication link such as, for example, a wireless connection, cable connection or any other means capable of allowing communication to occur between the components.

Figure 3:
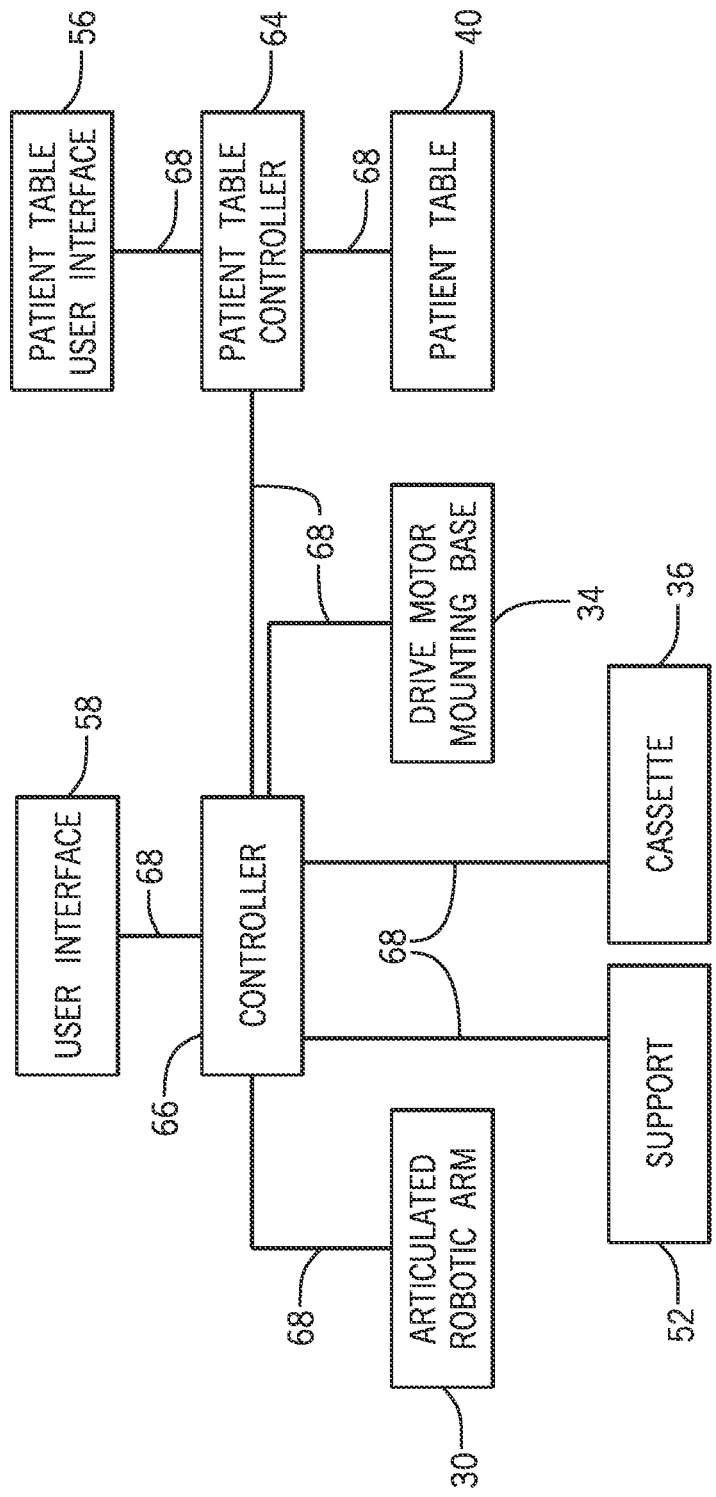
FIG. 3 is a block diagram of a system for controlling a position of an articulated robotic arm in a catheter procedure system in accordance with an embodiment.

FIG. 3 is a block diagram of a system for controlling a position of an articulated robotic arm in a catheter procedure system in accordance with an embodiment. Control console 54 (shown in FIG. 2) includes a controller (or first controller) 66 and patient table 40 (shown in FIG. 2) includes a patient table controller (or second controller) 64. Controller 66 and patient table controller 64 may be electronic control units suitable to provide the various functionalities described herein. Controller 66 is in communication with user interface 58, articulated robotic arm 30, support 52, drive motor mounting base 34 and cassette 36 via for example, communication links 68. In one embodiment, controller 66 may be located within control console 54 or in other embodiments, controller 66 may be located remotely from control console 54. Patient table controller 64 is in communication with patient table user interface 56 and patient table 40 via, for example, communication links 68.

Patient table controller 64 is also in communication with controller 66 via a communication link 68. Communication links 68 may be wired or wireless connections. Communication links 68 may also represent communication over a network. Patient table controller 64 is configured to generate control signals in response to a user's interaction with patient table user interface 56. In one embodiment, patient table controller 64 generates control signals to control the movement and position of the patient table 40 based on user input. The patient table controller 64 is also configured to transmit the control signals indicating the movement of the patient table 40 to the controller 66. In one embodiment, controller 66 may then automatically adjust the position of the articulated robotic arm 30 based on the control signal received from the patient table controller 64 so the articulated robotic arm 30 is in the proper orientation with respect to the patient table 40. As discussed above with respect to FIG. 2, the position of the patient table 40 and articulated robotic arm 30 may be adjusted in horizontal, vertical and transverse directions. In another embodiment, controller 66 may then automatically adjust the position of the support 52 (or a moveable portion of support 52) based on the control signal received from the patient table controller 64 so the articulated robotic arm 30 is in the proper orientation with respect to the patient table 40. The position of the support 52 may be adjusted in both the horizontal and vertical directions.

Figure 4:
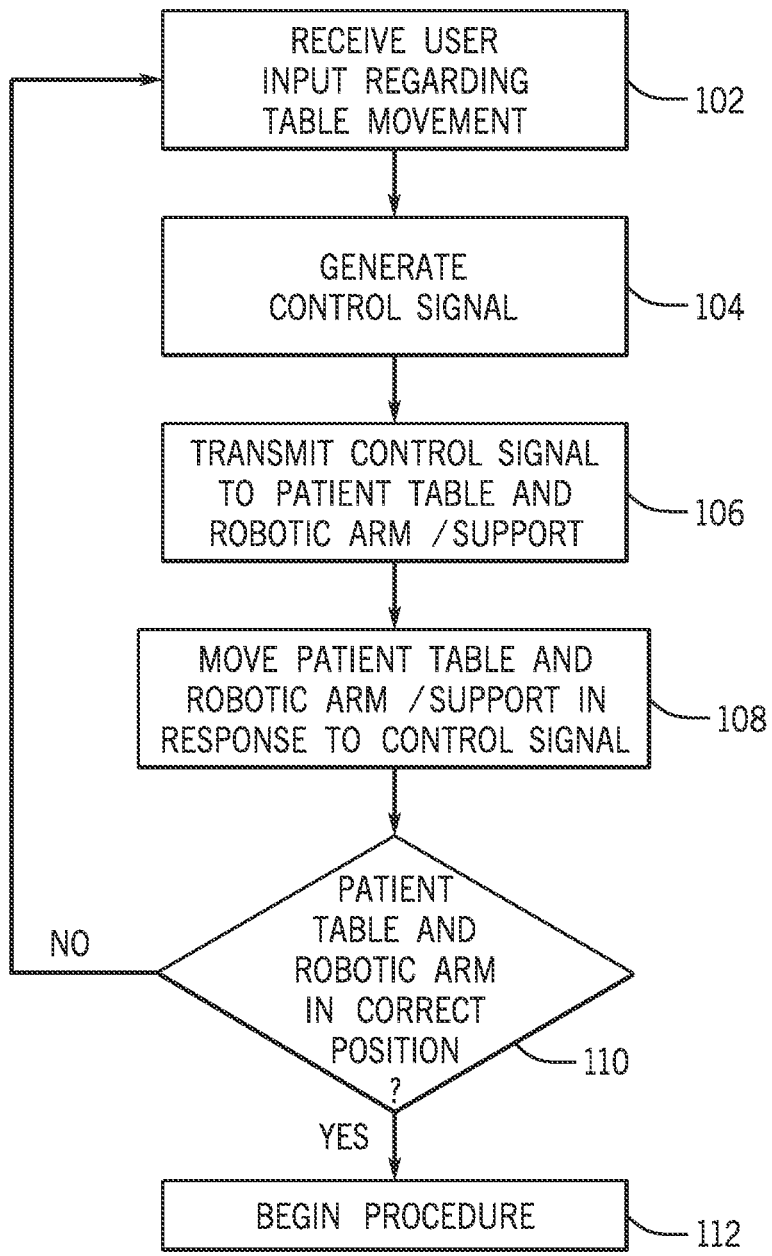
FIG. 4 illustrates a method for controlling a position of an articulated robotic arm in a catheter procedure system in accordance with an embodiment.

FIG. 4 illustrates a method for controlling a position of an articulated robotic arm in a catheter procedure system in accordance with an embodiment. At block 102, a user input is received via, for example, patient table user interface 56, indicating movement of the patient table 40. A control signal is generated at block 104 by, for example, patient table controller 64 and transmitted to the patient table and to either the articulated robotic arm or the support. At block 108, the patient table and either the articulated robotic arm or the support are automatically moved in response to the control signal. If the patient table and articulated robotic arm are in the correct position at block 110, the user may proceed with the catheter based medical procedure at block 112. If the patient table and articulated robotic arm are not in the correct position at block 110, the process returns to block 102 and additional user inputs may be received to further adjust the position of the patient table and articulated robotic arm.

Figure 5:
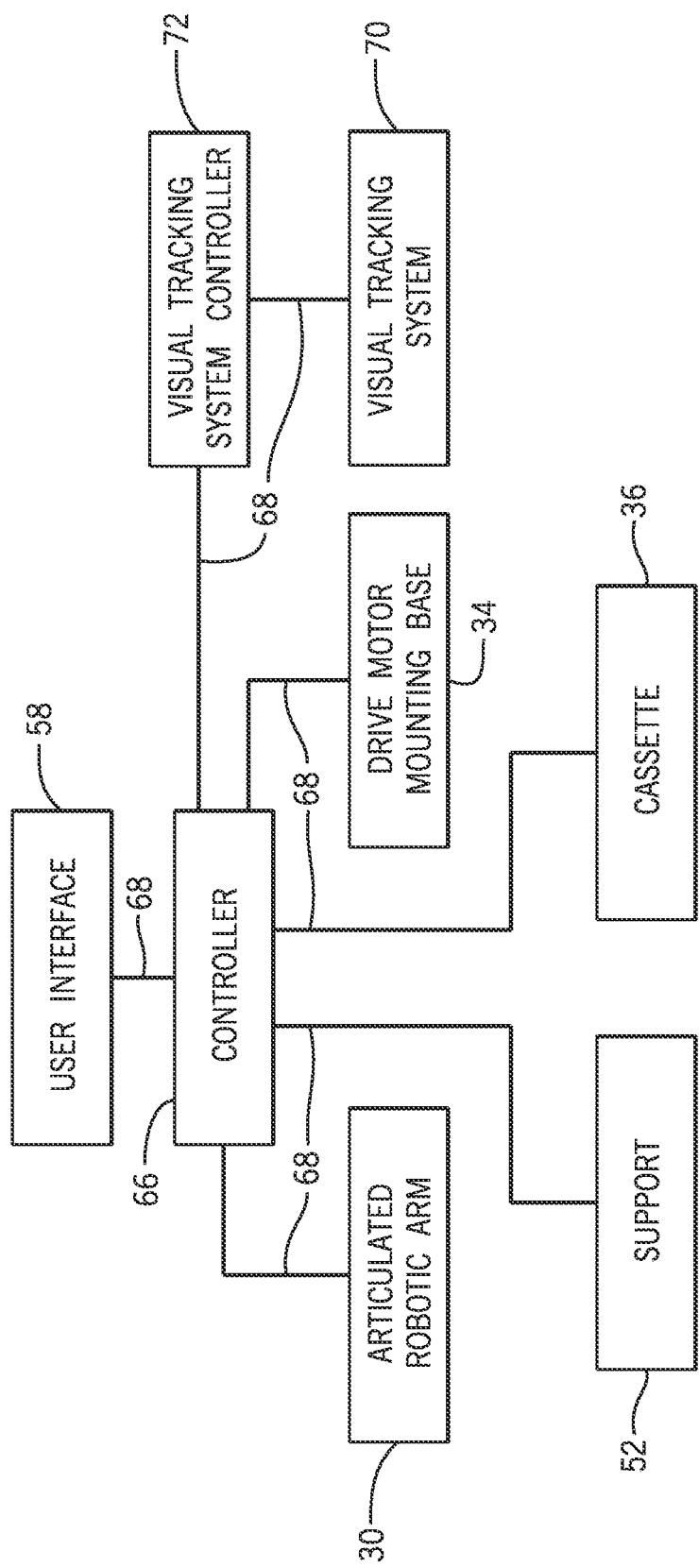
FIG. 5 is a block diagram of a system for controlling a position of an articulated robotic arm including a visual tracking system in accordance with an embodiment.

In another embodiment, a visual tracking system may be used to track the movement of the patient table and provide a control signal to automatically adjust the position of the support or the articulated robotic arm so that the articulated robotic arm is in the proper orientation with respect to the patient table. FIG. 5 is a block diagram of a system for controlling a position of an articulated robotic arm including a visual tracking system in accordance with an embodiment. A control console (such as control console 54 shown in FIG. 2) includes a controller 66. A visual tracking system 70 includes a visual tracking system controller 72. Visual tracking system 70 may be any device capable of visually tracking the movement of the patient table 40 (shown in FIG. 2) such as one or more video cameras. The one or more video cameras may be positioned in proximity to the patient table. Video signals may be provided from, for example, the cameras to the visual tracking system controller 72 and the controller 72 may generate a control signal to indicate the movement of the patient table.

The visual tracking system controller 72 is in communication with controller 66 via a communication link 68. Communication links 68 may be wired or wireless connections. Communication links 68 may also represent communication over a network. The visual tracking system controller 72 is configured to transmit the control signal indicating the movement of the patient table to the controller 66. In one embodiment, controller 66 may then automatically adjust the position of the articulated robotic arm 30 based on the control signal received from the visual tracking system controller 64 so the articulated robotic arm 30 is in the proper orientation with respect to the patient table 40. As discussed above, the position of the patient table 40 and articulated robotic arm 30 may be adjusted in horizontal, vertical and transverse directions. In another embodiment, controller 66 may then automatically adjust the position of the support 52 (or a moveable portion of support 52) based on the control signal received from the patient table controller 64 so the articulated robotic arm 30 is in the proper orientation with respect to the patient table 40. The position of the support 52 may be adjusted in both the horizontal and vertical directions.

Figure 6:
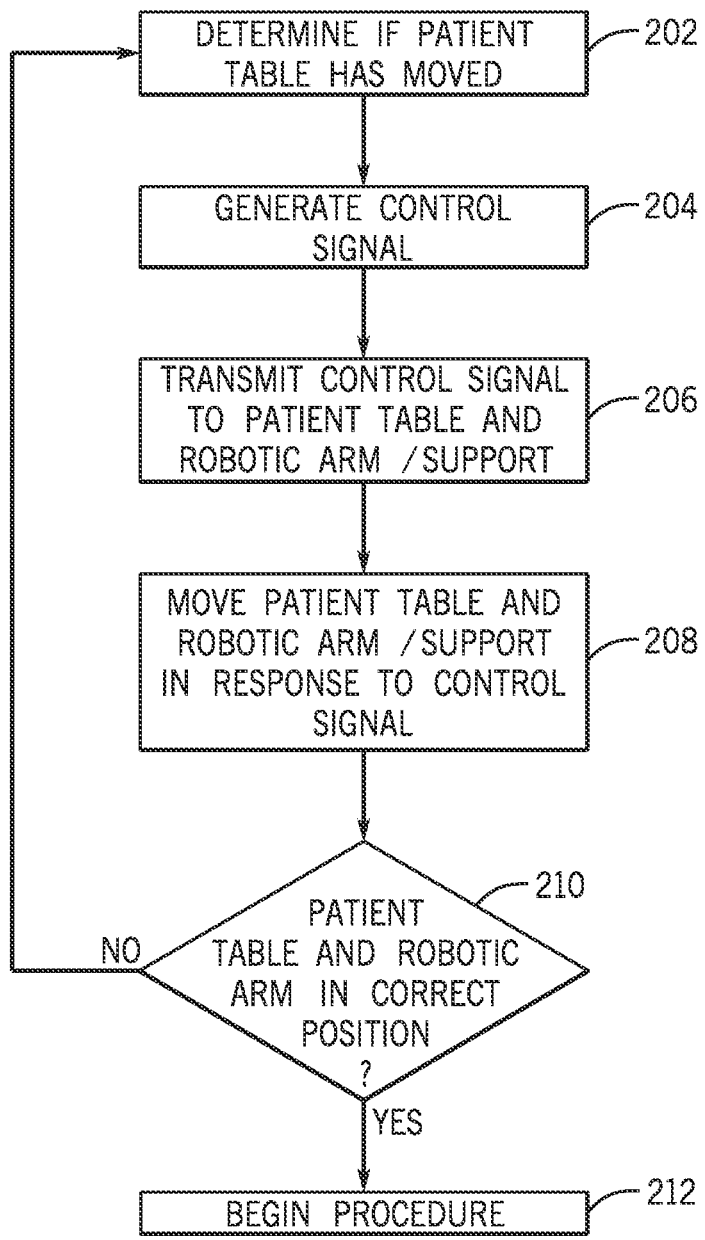
FIG. 6 illustrates a method for controlling a position of an articulated robotic arm in a catheter procedure system in accordance with an embodiment.

FIG. 6 illustrates a method for controlling a position of an articulated robotic arm in a catheter procedure system in accordance with an embodiment. At block 202, it is determined if the patient table has been moved, for example, using a visual tracking system 70. In one embodiment, the visual tracking system may include one or more cameras positioned in proximity to the patient table. A control signal is generated at block 204 by, for example, visual tracking system controller 72 and transmitted to the patient table and to either the articulated robotic arm or the support. At block 208, the patient table and either the articulated robotic arm or the support are automatically moved in response to the control signal. If the patient table and articulated robotic arm are in the correct position at block 210, the user may proceed with the catheter based medical procedure at block 212. If the patient table and articulated robotic arm are not in the correct position at block 210, the process returns to block 202.

Figure 7:
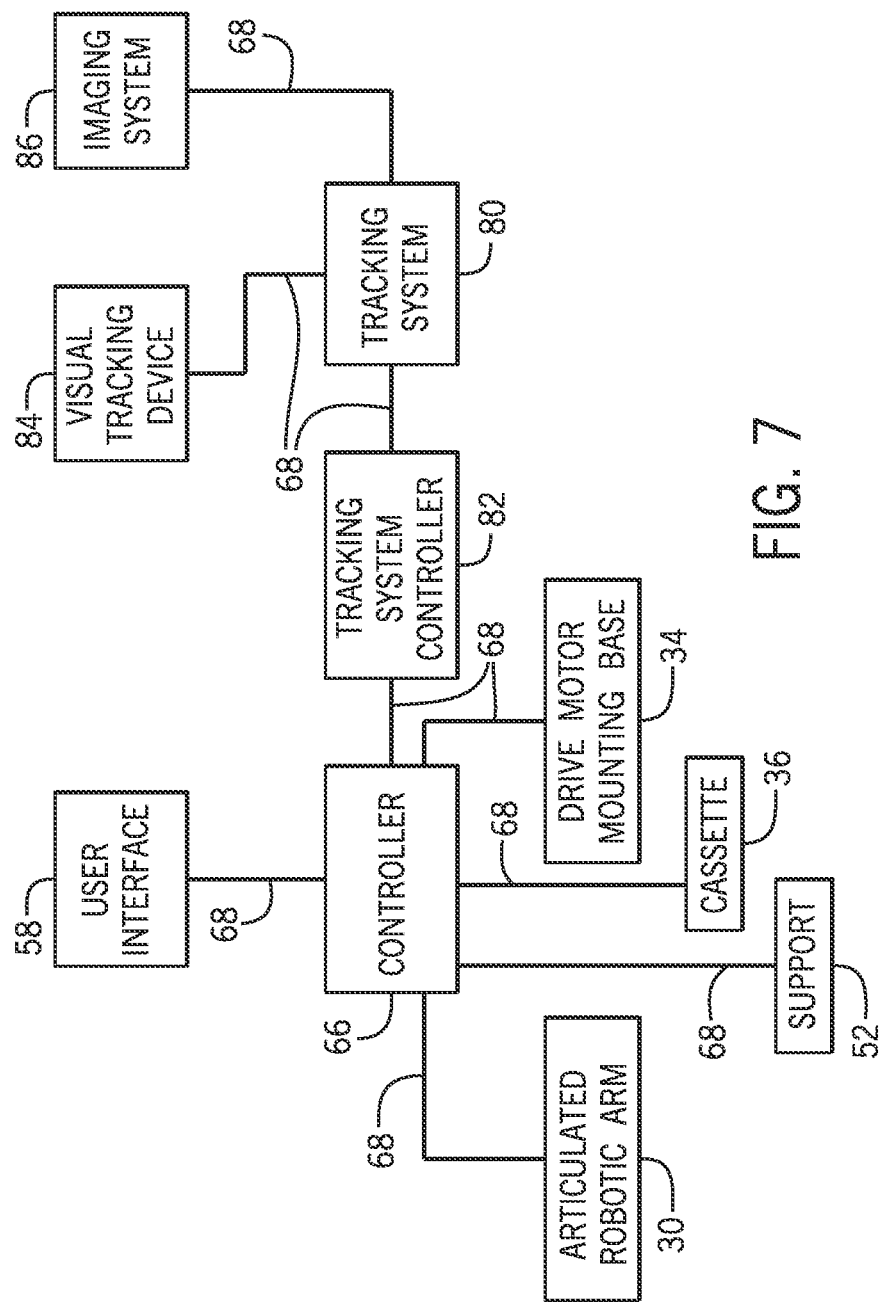
FIG. 7 is a block diagram of a system for controlling the position of an articulated robotic arm in a catheter procedure system in accordance with an embodiment.

In other embodiments, a tracking system may be used to track the position of the patient table, a patient on the patient table or a device used in the catheter procedure system and to control or adjust the position of the articulated robotic arm so that the articulated robotic arm is in the proper orientation with respect to the patient table and/or the patient. FIG. 7 is a block diagram of a system for controlling the position of an articulated robotic arm in a catheter procedure system in accordance with an embodiment. A control console (such as control console 54 shown in FIG. 2) includes a controller 66 that is in communication with user interface 58, articulated robotic arm 30, support 52, drive motor mounting base 34 and cassette 36 via, for example, communication links 68. In one embodiment, controller 66 may be located within control console 54 or in other embodiments, controller 66 may be located remotely from control console 54. The articulated robotic arm 30 may mounted to a support 52 as described above with respect to FIGS. 1A-6 or as further described below with respect to FIGS. 8-20. The support 52 may be any structure to which the articulated robotic arm 30 may be mounted such as, for example, a table, a cart with wheels, a surface located above the patient table and patient (e.g., a ceiling), a floor, a wall, etc. The drive motor mounting base 34 and the cassette 36 form a drive assembly and are configured to control and drive elongated medical devices used in the catheter procedure system. In one embodiment, the drive motor mounting base 34 and cassette 36 are mounted to a distal end of the articulated robotic arm 30. In another embodiment, a portion or the entirety of the drive motor mounting base 34 and cassette 36 are integrated into the articulated robotic arm 30. Controller 66 is in communication with the articulated robotic arm 30, support 52, drive motor mounting base 34 and cassette 36 to provide control signals to control various functions of the articulated robotic arm 30, support 52, drive motor mounting base 34 and cassette 36.

A tracking system 80 is in communication with the controller 66. In one embodiment, tracking system 80 includes a tracking system controller 82. In another embodiment, tracking system 80 may not include a separate controller 82 and the functionality of tracking system controller 82 may be included in controller 66. Controller 66 may be in communication with tracking system 80 and/or tracking system controller 82 via a communication link 68. Communication links 68 may be wired or wireless connections. Communication links 68 may also represent communication over a network.

In one embodiment, tracking system 80 is a measurement system that measures or determines the movement or amount of change in position of the patient table. For example, tracking system 80 may include one or more encoders on or in the patient table or in proximity to the patient table that are configured to measure or detect the position of the patient table. The encoder(s) may provide the position information to the tracking system controller 82 or to controller 66. In another embodiment, the tracking system 80 is a measurement system that determines changes in position of a fiducial target on the patient table or on the patient. For example, a visual tracking device 84 (e.g., a camera or cameras) may be coupled to the tracking system 80 and used to track or measure the position of an optical target, such as for example, light emitting diodes (LED's) or other type of mark or target that may be detected by a visual tracking device. In another example, an imaging system 86 (for example, a fluoroscopic x-ray system utilized by the catheter procedure system during a catheter procedure) may be coupled to the tracking system 80 and used to track or measure the position of a fiducial target configured to be detectable by the imaging system 86 (e.g. anatomy devices or an intentional target placed in a field). The tracking system 80 provides the position or measurement information to the tracking system controller 82 or to controller 66.

Figure 8:
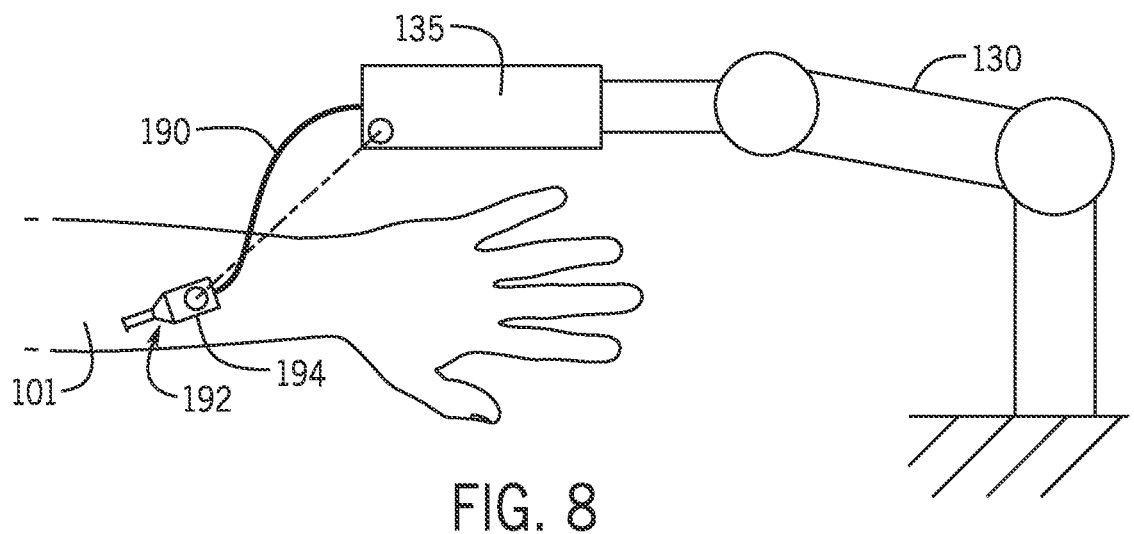
FIG. 8 is a schematic diagram of a catheter procedure system with a system for tracking an introducer in accordance with an embodiment.

In another embodiment, the visual tracking device 84 or imaging system 86 may be used to track or measure the position of a device used in the catheter procedure system (e.g., a distal or proximal end of the device). For example, an introducer at an access point into the patient may be tracked by tracking system 80. FIG. 8 is a schematic diagram of a catheter procedure system with a system for tracking an introducer in accordance with an embodiment. FIG. 8 shows an articulated robotic arm 130 with a drive assembly 135 located at a distal end of the articulated robotic arm 130 proximate to a patient 101. The drive assembly 135 is configured to control and drive elongated medical devices used in the catheter procedure system. In one embodiment, the drive assembly 135 is mounted to the distal end of the articulated robotic arm 130. In another embodiment, a portion or the entirety of the drive assembly 135 is integrated into the articulated robotic arm 130. In one embodiment, the drive assembly 135 may include a drive motor mounting base 34 and a cassette 36 as described above with respect to FIG. 2. An introducer 192 is used at an access point to provide access to the patient (e.g., an artery) for the elongated medical device 190 (e.g., a guide catheter, guide wire, etc.). A proximal end or hub 194 may include a fiducial marker such as a field coil, that may be tracked by a visual tracking device 84 (shown in FIG. 7) or an imaging system 86 (shown in FIG. 7). Referring again to FIG. 7, the tracking system 80 provides the position information for the introducer 192 to the tracking system controller 82 or to controller 66.

Tracking system controller 82 is configured to generate a control signal based on the position, change in position or measurement information from the tracking system 80. Tracking system controller 82 is also configured to transmit the control signal to the controller 66. In one embodiment, controller 66 may then automatically adjust the position of the articulated robotic arm 30 based on the control signal received from the tracking system controller 82 so the articulated robotic arm 30 is in the proper orientation with respect to the patient table 40 or the patient. As discussed above, the position of the articulated robotic arm 30 may be adjusted in the horizontal, vertical and transverse directions. In another embodiment, controller 66 may then automatically adjust to position of the support 52 (or a moveable portion of support 52) based on the control signal received from the tracking system controller 82 so the articulated robotic arm 30 is in the proper orientation with respect to the patient table 40 or to the patient. The position of the support may be adjusted on both the horizontal and vertical directions. In one example, the support 52 is a cart with wheels and the control signal is used to control movement of the wheels to adjust the position of the support 52. In another embodiment, controller 66 may be configured to generate a control signal based on the position, change in position or measurement information from the tracking system 80. The controller 66 may use the control signal to automatically adjust the position of the articulated robotic arm 30 so the articulated robotic arm 30 is in the proper orientation with respect to the patient table 40 or the patient. In another embodiment, controller 66 may automatically adjust to position of the support 52 (or a moveable portion of support 52) using the control signal so the articulated robotic arm 30 is in the proper orientation with respect to the patient table 40 or to the patient. Controller 66 may also be configured to identify a fault or error in tracking the movement and position of the patient table (e.g., using the methods described herein) and to generate and provide a control signal to the patient table 40 to lock the patient table to prevent further movement. For example, controller 66 may be in communication with a patient table controller 64 (shown in FIG. 3).

Figure 9:
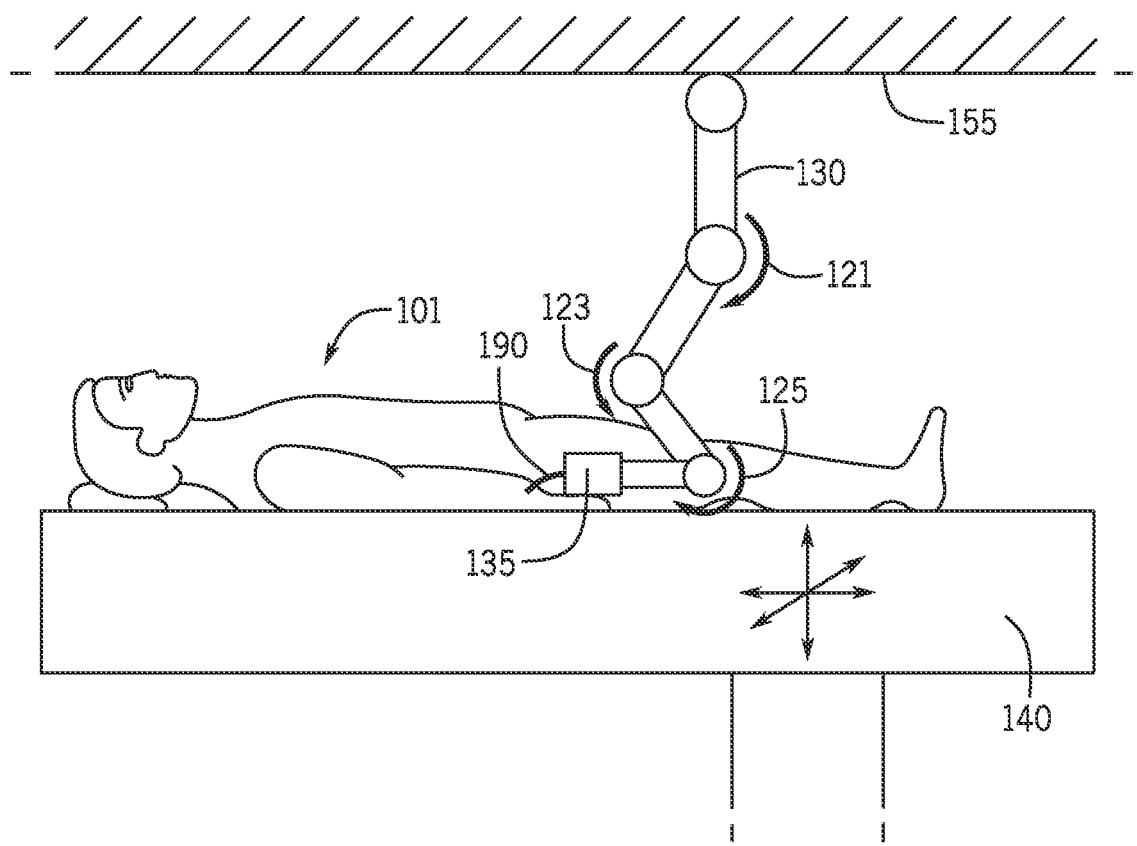
FIG. 9 is a schematic diagram of an articulated robotic arm for a catheter procedure system mounted to a ceiling in accordance with an embodiment.

In an embodiment, an articulated robotic arm 30 for a catheter procedure system may be mounted to a ceiling of the room (or other surface located above the patient table) in which the catheter procedure system is located for performing a catheter procedure. FIG. 9 is a schematic diagram of an articulated robotic arm for a catheter procedure system mounted to a ceiling in accordance with an embodiment. In FIG. 9, an articulated robotic arm 130 is mounted to a surface 155 of a ceiling or other surface located above the patient table 140 and the articulated robotic arm 130 extends generally downward towards the patient and/or patient table 140. The articulated robotic arm 130 includes a drive assembly 135 positioned on a distal end of the articulated robotic arm 130. The drive assembly 135 is configured to control and drive elongated medical devices used in the catheter procedure system. In one embodiment, the drive assembly 135 is mounted to the distal end of the articulated robotic arm 130. In another embodiment, a portion or the entirety of the drive assembly 135 is integrated into the articulated robotic arm 130. In one embodiment, the drive assembly 135 may include a drive motor mounting base 34 and a cassette 36 as described above with respect to FIG. 2. A position of the articulated robotic arm 130 may be adjusted in response to a position or change in position of a patient table 140, a patient 101 or a device in the catheter procedure system using any of the systems and methods described above with respect to FIGS. 1A to 8. For example, one or more joints of the articulated robotic arm 130 may be adjusted as shown, for example, by arrows 121, 123 and 125 based on the movement of the patient table in the horizontal, vertical or transverse directions. In another embodiment, the articulated robotic arm 130 may be mounted to a base (shown, foe example, in FIG. 18 below) attached to the surface located above the patient table and the base may include a first portion that is fixed and a second portion that is moveable. The moveable portion of the base may be configured to move relative to the fixed portion of the base. The position of the moveable portion of the base may then be adjusted based on the position or change in position of a patient table 140, a patient 101 or a device in the catheter procedure system. The position or change in position of the patient table 140, patient 101 or a device in the catheter procedure system may be determined using any of the systems and methods described above with respect to FIGS. 1A-8. Controller 66 may also be configured to identify a fault or error in tracking the movement and position of the patient table (e.g., using the methods described herein) and generate and provide a control signal to the patient table 40 to lock the patient table to prevent further movement. For example, controller 66 may be in communication with a patient table controller 64 (shown in FIG. 3).

Figure 10:
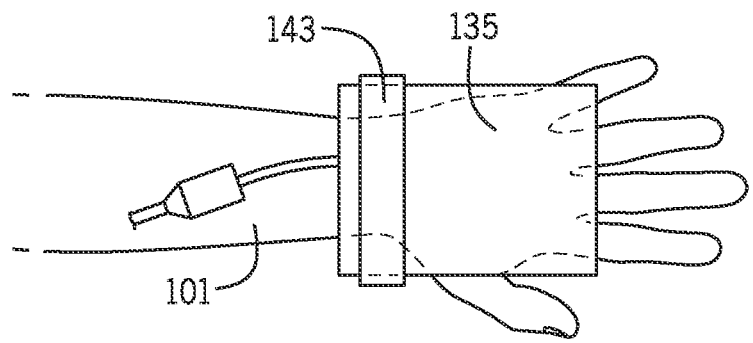
FIG. 10 is a schematic diagram of a drive system for a catheter procedure system mounted on a patient in accordance with an embodiment.
Figure 11:
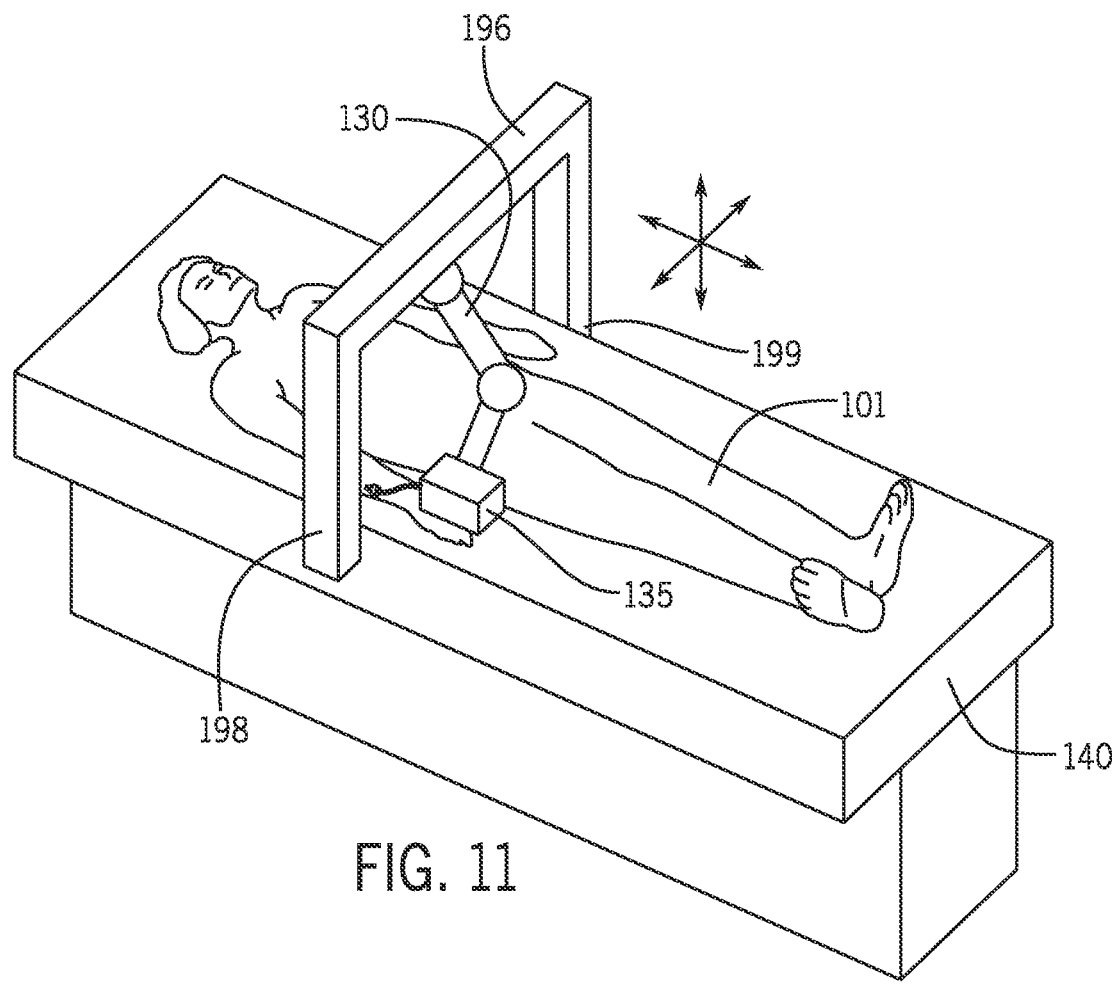
FIG. 11 is a schematic diagram of an articulated robotic arm for a catheter procedure system mounted to a gantry on a patient table in accordance with an embodiment.

In another embodiment, a drive assembly 135 may be mounted directly to a patient 101 s shown in FIG. 10. In FIG. 10, a drive assembly 135 is mounted or positioned on a patient 101 (e.g., a bond of the patient) and secured to the patient 101 using, for example, a strap 143. Alternatively, a drive assembly 135 may be positioned and secured to a leg of the patient. As mentioned above, the drive assembly 135 is configured to control and drive elongated medical devices used in the catheter procedure system. In one embodiment, the drive assembly, may include a drive motor mounting base 34 and a cassette 36 as described above with respect to FIG. 2. In yet another embodiment, an articulated robotic arm 130 and drive assembly 135 may be mounted to a gantry 196 as shown in FIG. 11. In FIG. 11, the gantry 196 is connected to a patient table 140 at a connection point 198 and a connection point 199. For example, the gantry 196 may be attached to a rail (not shown) on the side of the patient table 140. The gantry 196 is positioned over a patient and the patient table 140.

Figure 12:
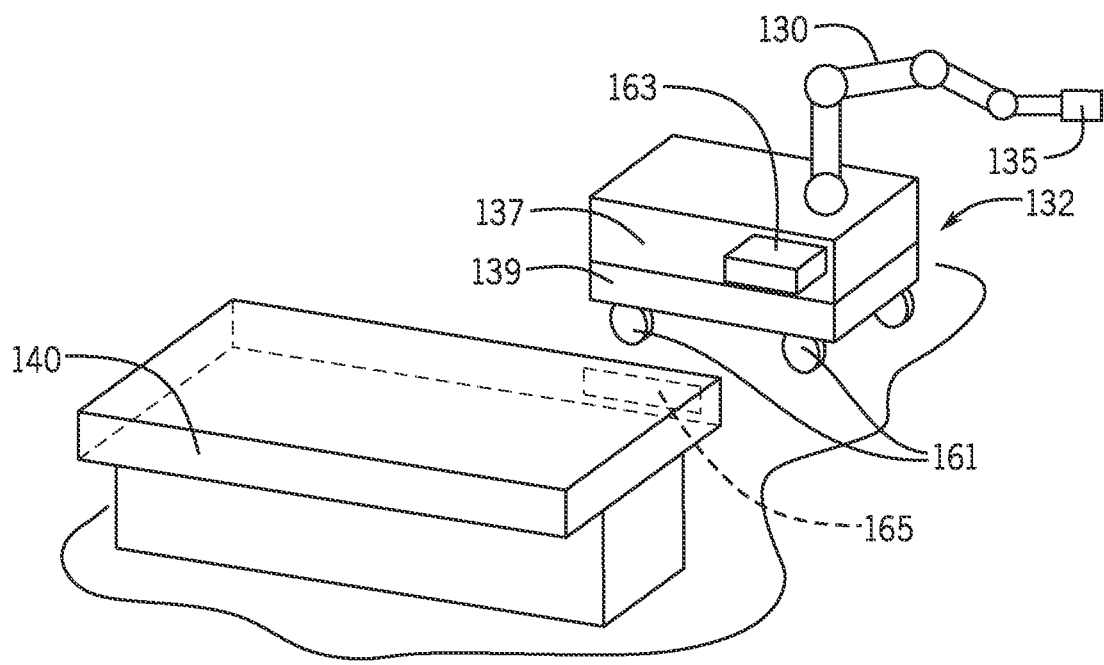
FIGS. 12-15 are schematic diagrams of a mechanical based tracking system for controlling the position of an articulated robotic arm in a catheter procedure system in accordance with an embodiment.
Figure 13:
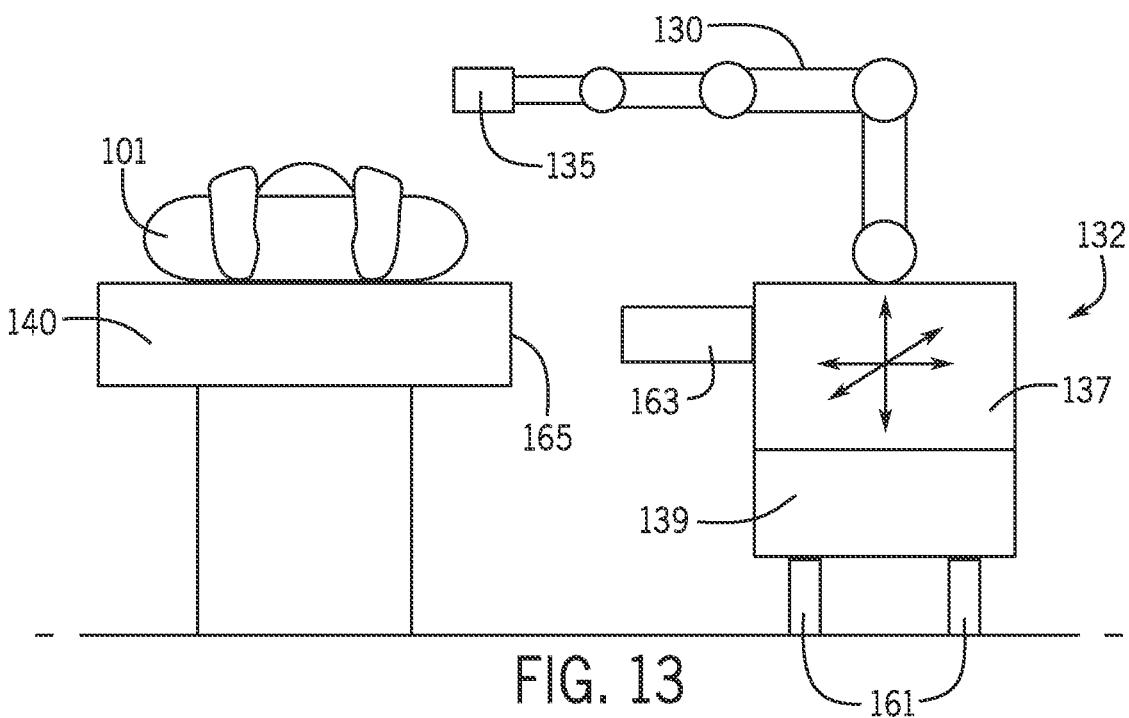
Figure 14:
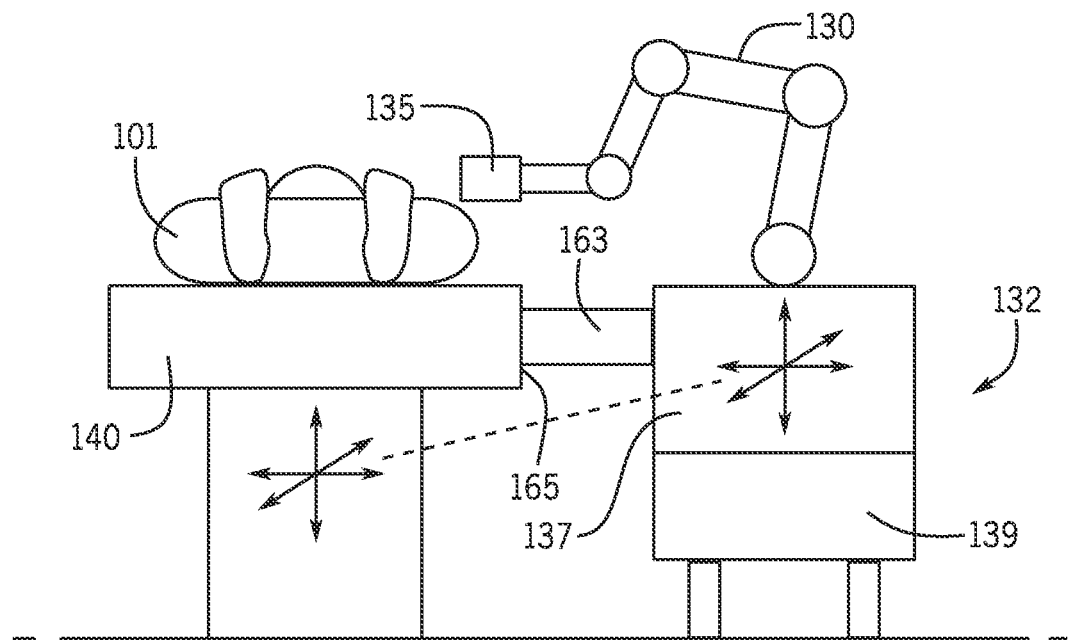
Figure 15:
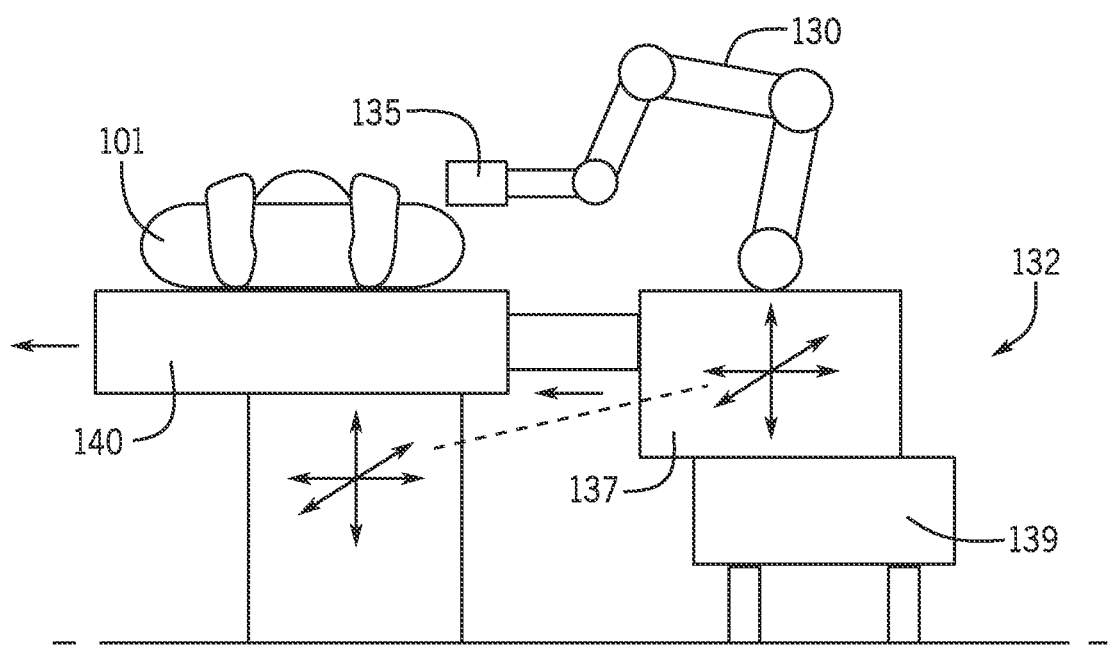

In other embodiments as described below with respect to FIGS. 12-20, the movement of the patient table 140 is tracked using a mechanical tracking system. FIGS. 12-15 are schematic diagrams of a mechanical based tracking system for controlling the position of an articulated robotic arm in a catheter procedure system in accordance with an embodiment. In FIGS. 12 and 13, an articulated robotic arm 130 with a drive assembly 135 are mounted to a cart 132 or other support having a set of wheels or casters 161 positioned on a bottom surface of the cart 132. The cart 132 includes a top portion 137 and a bottom portion 139. The top portion 137 is configured to move relative to the bottom portion 139 in horizontal and transverse directions. In one embodiment, the top portion 137 is also configured to move in a vertical direction relative to the bottom portion 139 of the cart 132. Alternatively, the top 137 and bottom 139 portions may move together in a vertical direction relative to a base and wheels 161. Cart 132 also includes a connector 163 configured to mechanically couple to a location 165 on a patient table. In one embodiment, the connector 163 on cart 132 may be a clamp and the location 165 on the patient table 140 may be a rail. Other known mechanisms may be used to attach the cart 132 to the patient table 140. FIG. 14 shows the cart 132 located proximate the patient table 140 and attached to the patient table 140 using connector 163 which is attached to a location 165 on the patient table. For example, a clamp may be connected to a rail on the patient table bed. The cart is locked in place by, for example, locking the wheels or casters 161. In another example, the cart may be locked in place by using padding on the floor. The cart is configured to have three translational degrees of freedom so the cart 132 may track movement or a change in position of the patient table so the articulated robotic arm 30 is in the proper orientation with respect to the patient table 40 or to the patient 101. Cart 132 may be provided with mechanisms such as, for example, slides or scissor mechanisms to provide the translational degrees of freedom (e.g., horizontal and vertical). In one embodiment, the mechanisms used to provide the movement of the cart may be locked when the cart is not attached to a patient table and unlocked when the cart is attached to a patient table. In another embodiment, the mechanisms may be shrouded to prevent interference with wires in the catheter procedure system. FIG. 15 shows an example horizontal translational movement of the patient table 140 that is tracked by the cart 132 via the mechanical connection provided by connector 163 to the location 165 on the patient table 140. In FIG. 15, the patient table is moved horizontally in the direction of arrow 173. The movement of the patient table 140 may be in response to, for example, a user input to a patient table user interface (not shown) indicating the desired change in position of the patient table 140. The top portion 137 of the cart 132 moves in the same horizontal direction, indicated by arrow 175, with the patient table via the mechanical connection of connector 163 to the patient table 140 at location 165. Accordingly, the cart 132 is able to move with the patient table 140 along the horizontal direction. The cart 132 may also move with the patient table 140 in a vertical direction (not shown).

Figure 16:
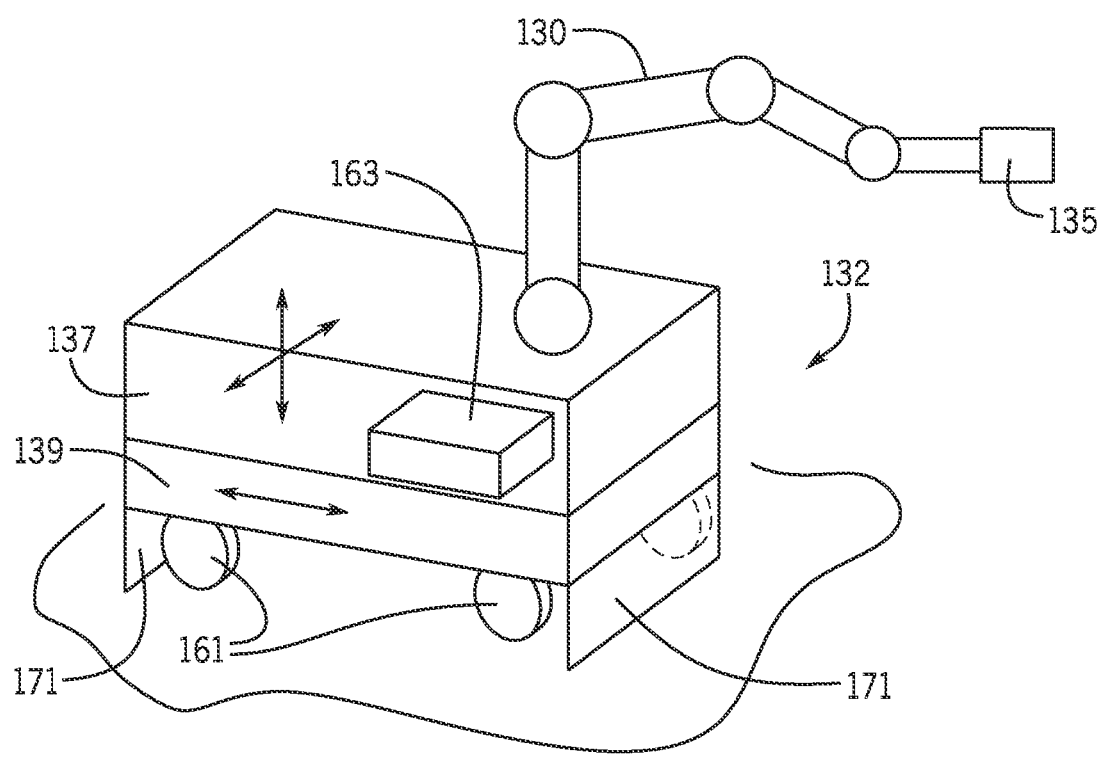
FIG. 16 is a schematic diagram of a mechanical based tracking system for controlling the position of an articulated robotic arm in a catheter procedure system in accordance with an embodiment.

In another embodiment, the movement along the horizontal direction or degrees of freedom is provided using the wheels or casters 161 of the cart 132. FIG. 16 is a schematic diagram of a mechanical based tracking system for controlling the position of an articulated robotic arm in a catheter procedure system in accordance with an embodiment. In FIG. 16, the wheels or casters 162 are free to move and when the cart 132 is attached to the patient table 140 allow the cart to track the movement or change in position of the patient table as described above. Accordingly, the cart 132 is able to move in a horizontal direction with the patient table 140 using the wheels 161. In one embodiment, a shroud 171 may be provided between the bottom portion of the cart 139 and the floor to prevent the wheels 161 from rolling over wires or hoses. In addition, a barrier, for example, padding, may be provided on the floor to limit the range of movement of the cart to a set space. Vertical movement of the cart 132 may be provided by mechanisms such as, for example, slides or scissor mechanisms as described above with respect to FIGS. 12-15. The cart 132 may also move with the patient table 140 in a vertical direction (not shown).

Figure 17:
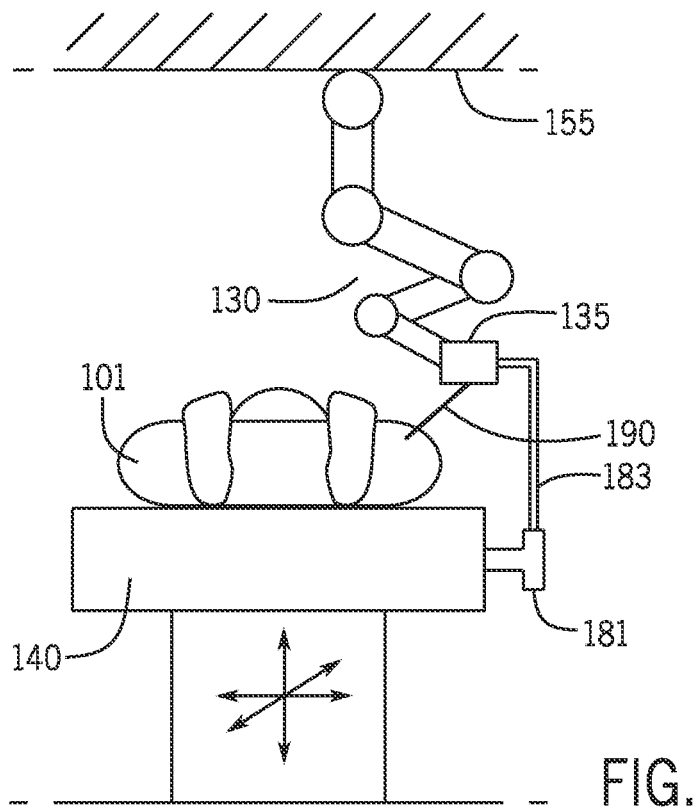
FIG. 17 is a schematic diagram of a mechanical based tracking system for controlling the position of an articulated robotic arm in a catheter procedure system in accordance with an embodiment.
Figure 18:
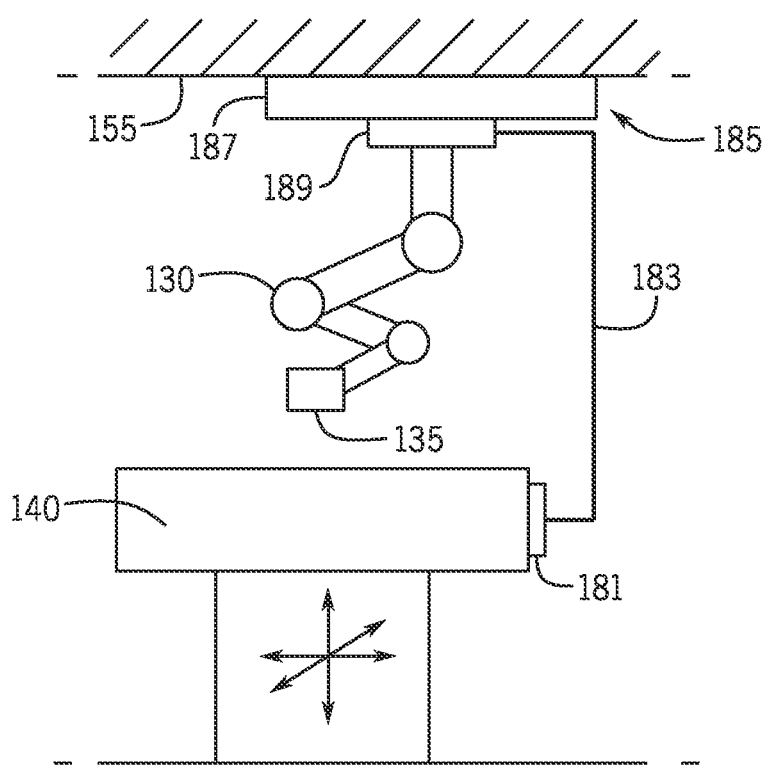
FIG. 18 is a schematic diagram of a mechanical based tracking system for controlling the position of an articulated robotic arm in a catheter procedure system in accordance with an embodiment.

FIG. 17 is a schematic diagram of a mechanical based system for controlling the position of an articulated robotic arm un a catheter procedure system in accordance with an embodiment. In FIG. 17, an articulated robotic arm 130 and drive assembly 135 are mounted to a surface 155 of a ceiling or other surface located above the patient table 140. A connector 183 is coupled to the articulated robotic arm 130 or drive assembly 135. The connector 183 is connected to a location on the patient table 140, for example, a rail 181. In one embodiment, the connector 183 may be a clamp that may be attached to the rail 181. The connector 183 provides a mechanical connection that causes the articulated robotic arm 130 to move or change position with the patient table 140 as the patient table 140 moves or changes position so that the articulated robotic arm 130 and drive assembly 135 are in the proper orientation with respect to the patient table 140 and/or patient 101. For example, one or more joints of the articulated robotic arm 130 may change position in response to the movement of the patient table 104 and connector 183. In an alternative embodiment, shown in FIG. 18, the articulated robotic arm 130 is mounted to a support or base 185 positioned on a surface 155 of a ceiling or other surface located above the patient table 140. Support 185 includes a first portion 187 an second portion 189. The second portion 189 may be configured to move relative to the first portion 187 in horizontal, vertical and transverse directions. A connector 183 is coupled to the second portion 189 of the support 185. The connector 183 is connected to a location on the patient table 140, for example, a rail 181. In one embodiment, the connector 183 may be a clamp that may be attached to the rail 181. The connector 183 provides a mechanical connection that causes the second portion 189 of the support 185 to move or change position with the patient table 140 as the patient table 140 moves or changes position so that the articulated robotic arm 130 and drive assembly 135 are in the proper orientation with respect to the patient table 140 and/or patient 101. In an alternative embodiment as discussed above with respect to FIG. 9, the position of the second portion 189 of the support or base 185 may be adjusted using a control signal generated based on the position or change in position of a patient table 140, a patient 101 or a device in the catheter procedure system.

Figure 19:
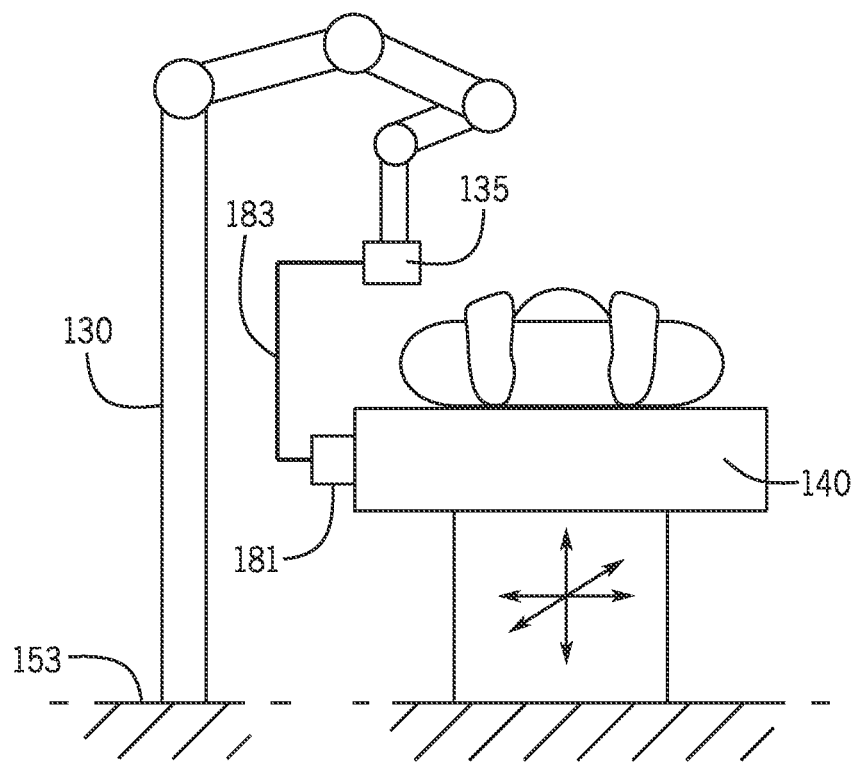
FIG. 19 is a schematic diagram of a mechanical based tracking system for controlling the position of an articulated robotic arm in a catheter procedure system in accordance with an embodiment.
Figure 20:
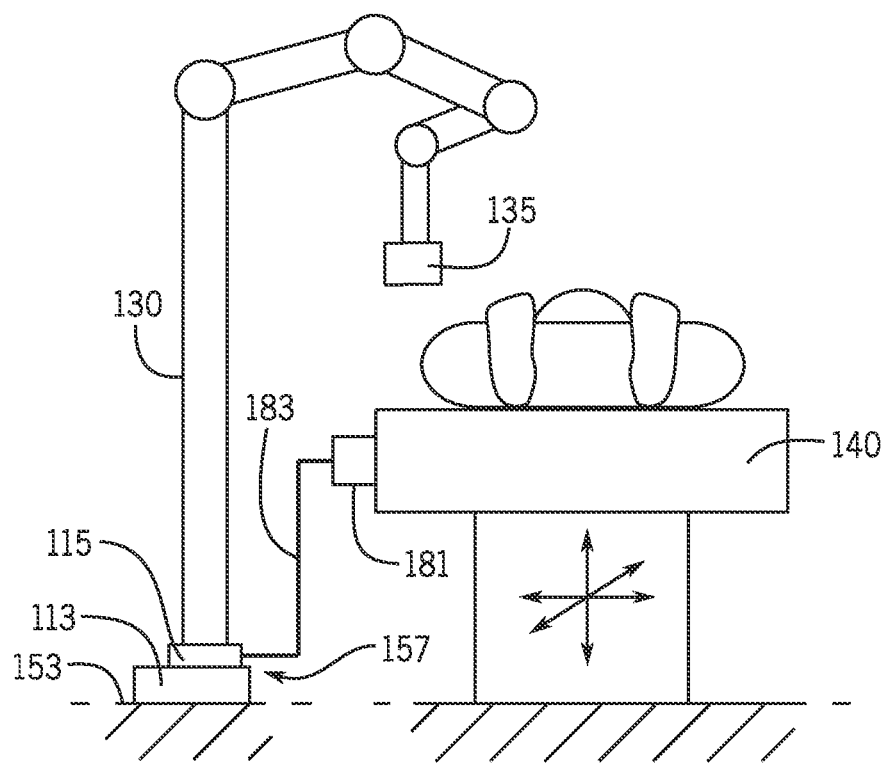
FIG. 20 is a schematic diagram of a mechanical based tracking system for controlling the position of an articulated robotic arm in a catheter procedure system in accordance with an embodiment.

FIG. 19 is a schematic diagram of a mechanical based system for controlling the position of an articulated robotic arm un a catheter procedure system in accordance with an embodiment. In FIG. 19, an articulated robotic arm 130 and drive assembly 135 are mounted to a surface 153 of a floor. A connector 183 is coupled to the articulated robotic arm 130 or drive assembly 135. The connector 183 is connected to a location on the patient table 140, for example, a rail 181. In one embodiment, the connector 183 may be a clamp that may be attached to the rail 181. The connector 183 provides a mechanical connection that causes the articulated robotic arm 130 to move or change position with the patient table 140 as the patient table 140 moves or changes position so that the articulated robotic arm 130 and drive assembly 135 are in the proper orientation with respect to the patient table 140 and/or patient 101. For example, one or more joints of the articulated robotic arm 130 may change position in response to the movement of the patient table 140 and connector 183. In an alternative embodiment, shown in FIG. 20, the articulated robotic arm 130 is mounted to a support or base 157 positioned on a surface 153 of a floor. Support 157 includes a first portion 113 an second portion 115. The second portion 115 may be configured to move relative to the first portion 113 in horizontal, vertical and transverse directions. A connector 183 is coupled to the second portion 115 of the support 157. The connector 183 is connected to a location on the patient table 140, for example, a rail 181. In one embodiment, the connector 183 may be a clamp that may be attached to the rail 181. The connector 183 provides a mechanical connection that causes the second portion 115 of the support 157 to move or change position with the patient table 140 as the patient table 140 moves or changes position so that the articulated robotic arm 130 and drive assembly 135 are in the proper orientation with respect to the patient table 140 and/or patient 101. In an alternative embodiment as discussed above with respect to FIG. 9, the position of the second portion 115 of the support or base 157 may be adjusted using a control signal generated based on the position or change in position of a patient table 140, a patient 101 or a device in the catheter procedure system.

While only certain features of the invention have been illustrated and described herein, many modifications and changes will occur to those skilled in the art. It is, therefore, to be understood that the appended claims are intended to cover all such modifications and changes as fall within the true spirit of the invention. A number of features are disclosed herein. These features may be combined in multiple combinations such that features may be used alone or in any combination with any of the other features.

What is claimed is:
1. A system for controlling a position of an articulated robotic arm, the system comprising:
 a movable cart comprising:
  a locking mechanism to prevent adjustment of the position of the movable cart in response to an error; and
  at least one of a wheel and a caster positioned on a bottom surface of the movable cart, the movable cart including a top portion and a bottom portion, the top portion configured to move relative to the bottom portion in horizontal and transverse directions;
 a robotic catheter procedure system comprising:
  the articulated robotic arm mounted on the movable cart; and
  a controller coupled to the movable cart; and
 a tracking system coupled to the controller and configured to measure a change in a position of a patient table positioned proximate to and separate from the movable cart, wherein the controller is configured to automatically adjust a position of the top portion of the movable cart in at least one of a transverse direction or a horizontal direction based on the measured change in position of the patient table, and to generate a control signal to activate the locking mechanism based on an error received from the tracking system, and wherein the tracking system is configured to measure a change in position of a fiducial target provided on the patient table, the change in position of the fiducial target being indicative of the change in position of the patient table.

2. The system according to claim 1, wherein the tracking system generates a signal in response to the measured change in the position and transmits the signal to the controller.

3. The system according to claim 1, wherein the tracking system comprises at least one encoder.

4. The system according to claim 1, wherein the tracking system comprises a visual tracking device configured to track the fiducial target.

5. The system according to claim 4, wherein the fiducial target comprises at least one light emitting diode.

6. The system according to claim 1, wherein the fiducial target comprises at least one field coil.

7. A system for controlling a position of an articulated robotic arm, the system comprising:

a movable cart comprising:
- a locking mechanism to prevent adjustment of the position of the movable cart in response to an error; and
- at least one of a wheel and a caster positioned on a bottom surface of the movable cart, the movable cart including a top portion and a bottom portion, the top portion configured to move relative to the bottom portion in horizontal and transverse directions;

a robotic catheter procedure system comprising:
- the articulated robotic arm mounted on the movable cart; and
- a controller coupled to the movable cart;

a patient table user interface configured to control movement of a patient table positioned proximate to and separate from the movable cart; and a tracking system coupled to the controller and configured to measure a change in a position of the patient table;

a patient table controller coupled to the patient table user interface and the controller, the patient table controller programmed to:

transmit a control signal to the controller in response to a user input received by the patient table user interface, the user input instructing a change in position of the patient table, wherein the controller is configured to automatically adjust a position of the top portion of the movable cart in at least one of a transverse direction or a horizontal direction based on the change in position of the patient table, and to generate a second control signal to activate the locking mechanism based on an error received from the patient table controller, and wherein the tracking system is configured to measure a change in position of a fiducial target provided on the patient table, the change in position of the fiducial target being indicative of the change in position of the patient table.

8. The system according to claim 7, wherein the tracking system generates a signal in response to the measured change in the position and transmits the signal to the controller.

9. The system according to claim 7, wherein the tracking system comprises at least one encoder.

10. The system according to claim 7, wherein the tracking system comprises a visual tracking device configured to track the fiducial target.

11. The system according to claim 10, wherein the fiducial target comprises at least one light emitting diode.

12. The system according to claim 7, wherein the fiducial target comprises at least one field coil.

* * * * *